(12) United States Patent
Walborn

(10) Patent No.: US 8,505,871 B2
(45) Date of Patent: *Aug. 13, 2013

(54) ELECTRONICALLY ACTIVATED ACCESS VALVE

(75) Inventor: Jonathan Walborn, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/081,418

(22) Filed: Apr. 6, 2011

(65) Prior Publication Data

US 2011/0186139 A1   Aug. 4, 2011

Related U.S. Application Data

(62) Division of application No. 11/796,219, filed on Apr. 27, 2007, now Pat. No. 7,922,148.

(51) Int. Cl.
*F16K 51/00* (2006.01)

(52) U.S. Cl.
USPC ............... 251/128; 251/129.01; 251/149

(58) Field of Classification Search
USPC ........... 251/128, 129.01, 129.03, 149, 149.9; 439/194; 285/149.1–151.1
See application file for complete search history.

(56) References Cited

U.S. PATENT DOCUMENTS

| | | | | |
|---|---|---|---|---|
| 1,890,290 A * | 12/1932 | Hargreaves | ................... | 439/194 |
| 2,492,449 A * | 12/1949 | Tuller et al. | ................... | 425/170 |
| 3,253,245 A * | 5/1966 | Brandt | ................... | 439/191 |
| 3,321,177 A | 5/1967 | Fendel et al. | | |
| 3,339,632 A * | 9/1967 | Lewis | ................... | 166/335 |
| 3,649,949 A * | 3/1972 | McCarthy et al. | ............ | 439/194 |
| 3,773,186 A * | 11/1973 | Reno et al. | ................... | 213/1.3 |
| 3,992,565 A * | 11/1976 | Gatfield | ................... | 174/15.7 |
| 4,032,821 A * | 6/1977 | Keiser | ................... | 361/622 |
| 4,094,567 A * | 6/1978 | Karcher et al. | ............... | 439/194 |
| 4,302,064 A * | 11/1981 | Spinner | ................... | 439/198 |
| 4,438,996 A * | 3/1984 | Zehren | ................... | 439/137 |
| 4,605,268 A * | 8/1986 | Meador | ................... | 439/194 |
| 4,913,657 A * | 4/1990 | Naito et al. | ................... | 439/192 |
| 5,156,180 A | 10/1992 | Sturgis | | |
| 5,365,984 A * | 11/1994 | Simpson et al. | ............... | 141/387 |
| 5,683,118 A * | 11/1997 | Slocum | ................... | 285/119 |
| 6,089,539 A | 7/2000 | Kouda | | |
| 6,464,520 B2 * | 10/2002 | Saba | ................... | 439/191 |
| 6,510,608 B1 * | 1/2003 | Marshall et al. | ............... | 29/869 |
| 6,671,898 B1 | 1/2004 | Eggenberger et al. | | |
| 6,717,501 B2 * | 4/2004 | Hall et al. | ................... | 336/132 |
| 6,783,379 B2 * | 8/2004 | Kerscher et al. | ............... | 439/191 |
| 6,899,132 B2 | 5/2005 | Mikiya et al. | | |
| 6,973,867 B2 * | 12/2005 | Frisch et al. | ................... | 91/459 |
| 2006/0219970 A1 | 10/2006 | Budde | | |
| 2008/0216907 A1 * | 9/2008 | Smith, III | ................ | 137/614.04 |

* cited by examiner

*Primary Examiner* — John Bastianelli
(74) *Attorney, Agent, or Firm* — McDermott Will & Emery LLP

(57) ABSTRACT

An electrically activated access valve arrangement having a male connector, a female connector, and a valve. In certain embodiments, the male connector includes a conductive element, and the female connector includes contacts. Insertion of the male into the female connector completes a circuit and sends an electrical signal to the valve. This transitions the valve from the normally closed position to the opened position. In certain embodiments, the male connector has a connection port that connects to a connection port of the female connector. A pump, such as an infusion pump, sends an electrical signal through the connection ports, which causes the valve to transition from the normally closed position to the opened position. The electrically activatable valve of the connectors is prevented from opening if mated with conventional male and female luers.

2 Claims, 8 Drawing Sheets

ELECTRONICALLY ACTIVATED ACCESS VALVE

CROSS REFERENCE TO RELATED APPLICATIONS

This application is a divisional of U.S. patent application Ser. No. 11/796,219 filed on Apr. 27, 2007 and now issued as U.S. Pat. No. 7,922,148, the entire disclosure of which is hereby incorporated by reference.

TECHNICAL FIELD

The disclosed embodiments relate to an electrically activated access valve arrangement, and more particularly, to a male and female connection device that electrically activates an access valve, to be used in conjunction with fluid administration, such as intravenous fluid administration.

BACKGROUND

Luer connections are the typical way of attaching various medical devices such as syringes, catheters, and intravenous lines to one another. These lines are then generally connected to a patient via a catheter. In a typical luer connection, male and female connectors are mated together to form and secure the connection. Luer connections are widely used in the medical industry because they are quick and easy to assemble.

However, with this ease of use comes a high risk of error. For example, in high risk connections, such as epidural lines, the connection of an incorrect line can have serious consequences, including death, for the patient. There is a high risk of accidentally connecting the wrong lines because standard luer connectors are used for both intravenous fluid and epidural infusions. Also, additional lines are commonly found near bedsides of patients seeking medical care for a variety of ailments. Thus, a male connector intended for use with an intravenous line could be easily confused for one intended for use with an epidural line. This confusion can lead to a misconnection, resulting in medication or air erroneously being delivered into an unintended site, leading to serious complications.

Currently, precautions for misconnections include double-checking the connection prior to connecting the luers. Alternatively, the different connectors and their attached lines may be specially labeled. Labeling may be accomplished by placing colored tape on the tubing, or placing a color-coded marker on the connectors themselves.

While these precautionary measures attempt to solve the problems of misconnections, all of these precautions require an active, mitigating step. This can be problematic and unpractical for nurses and doctors who are often working in emergency situations and do not have the luxury of performing time-consuming cautionary steps.

Thus, there is a real need for a connection that ensures the line will remain closed until the correct connectors are connected. This will mitigate the risk of misconnecting male and female luers, and it requires no additional steps by hospital personnel to avoid misconnections.

SUMMARY

The above and other needs are met by the disclosed embodiments which provide an electrically activated access valve arrangement comprising a male connector, which includes a body, a distal end, a proximal end, and a fluid passage. A conductive element is located on the body. The conductive element is located such that it is external of the path of the fluid passage. The electrically activated access valve arrangement further comprises a female connector, comprising a body, a distal end, a proximal end, and an opening. When the male connector is inserted into the female connector, the opening is in fluid communication with the fluid passage. The female connector further comprises contacts. The electrically activated access valve arrangement also comprises a valve connected to the opening of the female connector. Upon full insertion of the male connector to the female connector, the conductive element of the male connector physically contacts the contacts of the female connector. This provides an electrical pathway for an electrical signal to be sent to the valve to transition the valve from a normally closed position to an opened position.

The earlier stated needs and others are met by still other disclosed embodiments which provide an electrically activated access valve arrangement comprising a male connector. The male connector comprises a body, a distal end, a proximal end, and a fluid passage. The male connector includes at least one connection port. The electrically activated access valve arrangement further comprises a female connector comprising a body, a distal end, a proximal end, and an opening. The opening is in fluid communication with the fluid passage when the male connector is inserted into the female connector. The female connector further comprises at least one connection port and a valve. The valve is electrically controllable to transition from a normally closed position to an opened position.

The foregoing and other features, aspects and advantages of the disclosed embodiments will become more apparent from the following detailed description and accompanying drawings.

DETAILED DESCRIPTION

It is contemplated that the subject matter described herein may be embodied in many forms. Accordingly, the embodiments described in detail below are the presently preferred embodiments, and are not to be considered as limitations.

The disclosed embodiments address problems related to the misconnection of male and female luer connection devices and the dire consequences misconnections may cause in time-critical situations. The disclosed embodiments solve these problems, at least in part, by providing an electrically activated access valve arrangement comprising a male connector, which includes a body, a distal end, a proximal end, and a fluid passage. A conductive element is located on the body. The conductive element is located such that it is external of the path of the fluid passage. The electrically activated access valve arrangement further comprises a female connector, comprising a body, a distal end, a proximal end, and an opening. When the male connector is inserted into the female connector, the opening is in fluid communication with the fluid passage. The female connector further comprises contacts. The electrically activated access valve arrangement also comprises a valve connected to the opening of the female connector. Upon full insertion of the male connector to the female connector, the conductive element of the male connector physically contacts the contacts of the female connector. This provides an electrical pathway for an electrical signal to be sent to the valve to transition the valve from a normally closed position to an opened position.

Other disclosed embodiments provide an electrically activated access valve arrangement comprising a male connector. The male connector comprises a body, a distal end, a proximal end, and a fluid passage. The male connector includes at least one connection port. The electrically activated access valve arrangement further comprises a female connector comprising a body, a distal end, a proximal end, and an opening. The opening is in fluid communication with the fluid passage when the male connector is inserted into the female connector. The female connector further comprises at least one connection port and a valve. The valve is electrically controllable to transition from a normally closed position to an opened position.

Figure 1A:
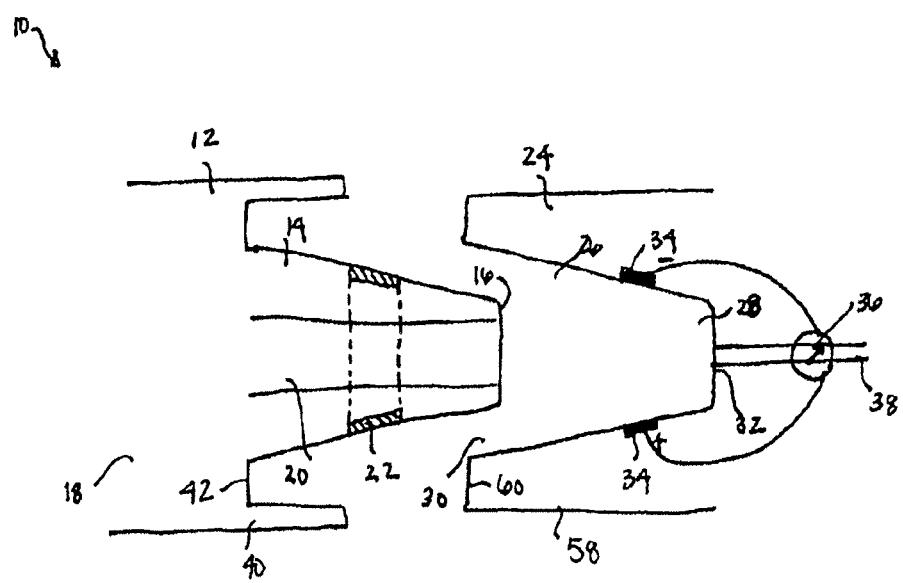
FIG. 1a is a cross-sectional view of one embodiment of male and female connectors with an electrically activated access valve, prior to connection.

FIG. 1a shows an electrically activated access valve arrangement 10, comprising a male connector 12, a female connector 24, and a valve 36. The male connector 12 comprises a body 14, a distal end 16, a proximal end 18, and a fluid passage 20. It should be noted that "distal" refers to the direction toward the patient. "Proximal" refers to the direction away from the patient, or toward the syringe or other collection or dispensing device, such as an intravenous (IV) bag. The body 14 is generally frustoconically shaped. A conductive element 22 is located on the body 14. The position of the conductive element 22 on the body 14, shown in FIG. 1, is such that it does not obstruct and is not in contact with the fluid passage 20. The fluid passage 20 may be surrounded by a barrier 44 (seen in FIG. 3), which would isolate the conductive element 22 from the fluid passage 20, thereby preventing possible complications. Further, the barrier 44 would ensure that there are no obstructions within the path of the fluid in the fluid passage 20.

Figure 1B:
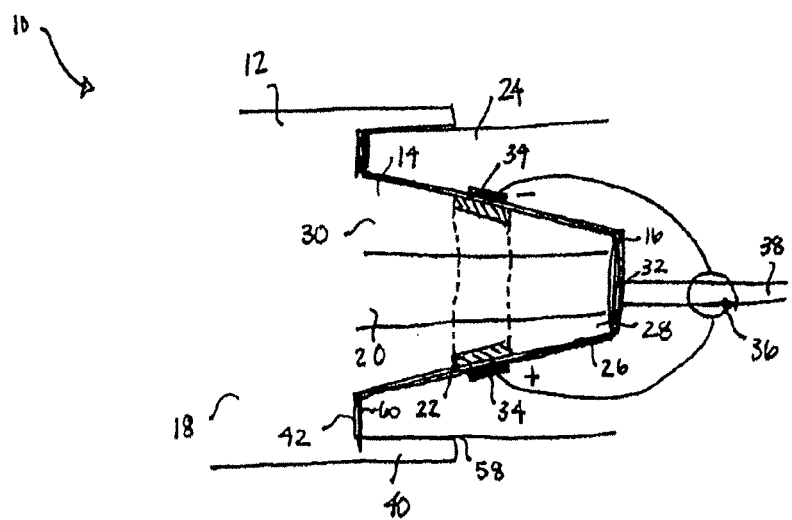
FIG. 1b is a cross-sectional view of the male and female connectors of FIG. 1a, after connection.

FIG. 1a also shows the female connector 24, comprising a body 26, a distal end 28, a proximal end 30, and an opening 32. The body 26 of the female connector 24 may be generally shaped to receive the frustoconical body 14 of the male connector 12. When the male connector 12 is inserted into the female connector 24, the opening 32 of the female connector 24 is in fluid communication with the fluid passage 20 of the male connector 12. The female connector 24 further comprises contacts 34, which may be located on the exterior of the body 26. The contacts 34 of the female connector 24 engage the conductive element 22 when the male connector 12 is fully inserted into the female connector 24, as depicted in FIG. 1b. When this engagement occurs, a circuit is completed. A power source (not shown) is connected to the contacts 34 to provide power to activate the valve 36. The power source can be external or located on the connector 24 itself.

The valve 36, as seen in FIG. 1a, is connected to the opening 32 of the female connector 24. A line 38 runs through the male and female connectors 12, 24, and through the valve 36. The line 38 will carry fluid to flow from a fluid source (not shown) to a patient. Normally, the valve 36 is in a closed position, as seen in FIG. 1a. However, when the conductive element 22 and contacts 34 are engaged, an electrical pathway is formed. The electrical pathway allows an electrical signal to be sent to the valve 36. This electrical signal causes the valve 36 to transition from the closed position to an opened position, allowing fluid to flow through the line 38. FIG. 1b shows the conductive element 22 and the contacts 34 engaged. This allows for the valve 36 to be in the opened position. If the male and female connectors 12, 24 are disengaged such that the circuit is broken, the electrical activation terminates, and the valve 36 will return to the closed position.

The electric activation of the valve 36 ensures that only the dedicated male connector 12, including the conductive element 22, can be connected to the female connector 24, in a manner that permits fluid flow, as this is the only connection that will cause the circuit to be completed and the valve 36 to open. Thus, as the female connector 24 is closer to the patient and likely connected to a patient catheter, the risk of connecting the wrong male connector 12 and wrong line is mitigated or eliminated. However, the male connector 12 may be used in connection with typical female luer connectors as well as the dedicated female connector 24.

Figure 2A:
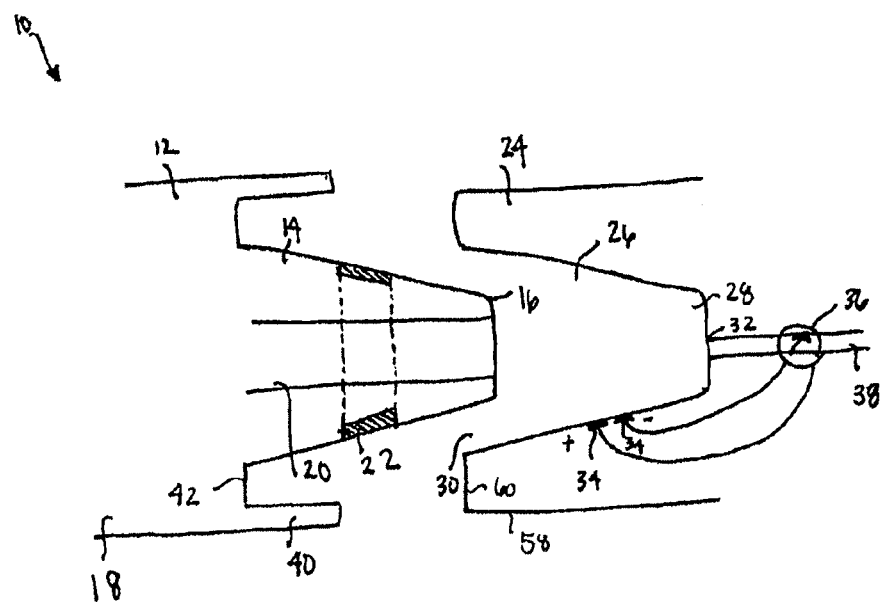
FIG. 2a is a cross-sectional view of another embodiment of male and female connectors with an electrically activated access valve, prior to connection.
Figure 2B:
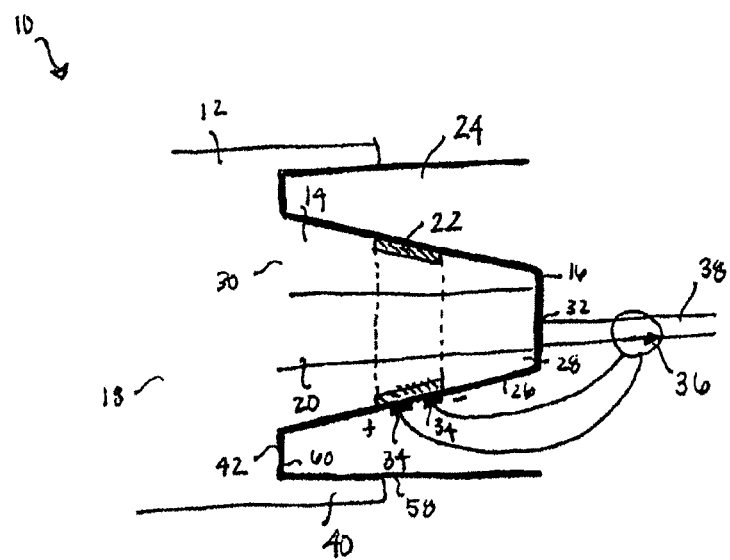
FIG. 2b is a cross-sectional view of the male and female connectors of FIG. 2a, after connection.

The contacts 34 of the female connector 24 may be located radially, around the circumference of the body 26, as seen in FIGS. 1a and 1b. It is contemplated that the contacts 34 may be aligned along the length of the body 26, shown in the embodiment of FIGS. 2a and 2b. If the contacts 34 are aligned along the length of the body 26, the conductive element 22 may be substantially wider such that it will come into contact with both the positive and negative contacts 34. The conductive element 22 may completely encircle the body 14 of the male connector 12, or it may be broken up into segments. In operation the embodiment of FIGS. 2a and 2b is the same as the embodiment of FIGS. 1a and 1b.

Figure 3:
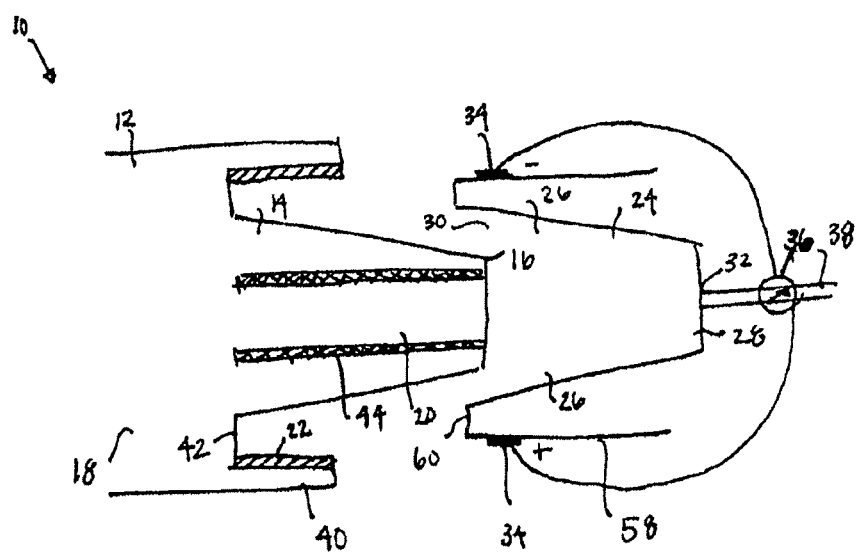
FIG. 3 is a cross-sectional view of another embodiment of male and female connectors with an electrically activated access valve.

In another embodiment, as shown in FIG. 3, the conductive element 22 is a band, located around a hub 40 of the male connector 12. This placement ensures the conductive element 22 will not interfere with the fluid passage 20. The hub 40 of the male connector essentially encircles the body 14 of the male connector 12. It also encircles a hub 58 of the female connector 24 when the male connector 12 is fully inserted into the female connector 24. FIG. 3 shows that if the conductive element 22 is located around the hub 40 of the male connector, the contacts 34 of the female connector 24 may be correspondingly arranged around the hub 58 of the female connector 24.

Figure 4:
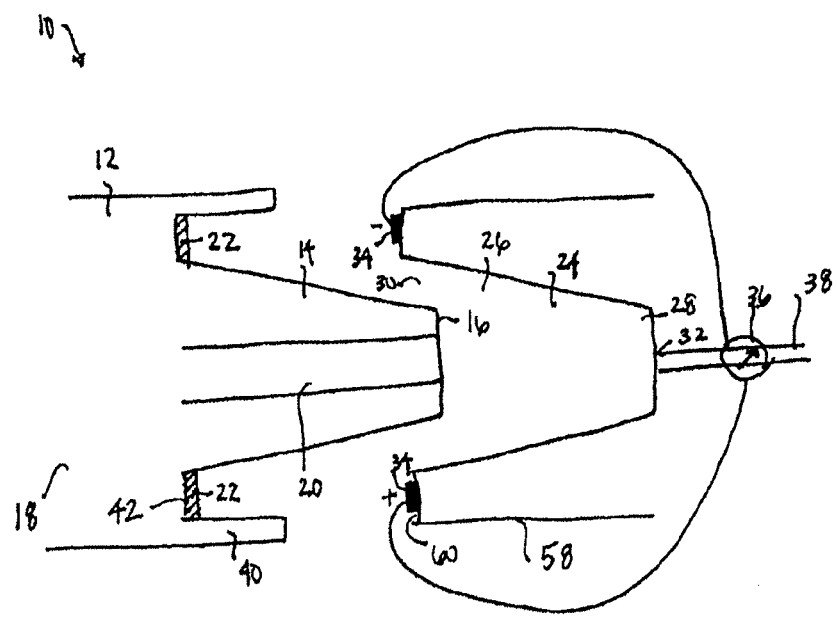
FIG. 4 is a cross-sectional view of another embodiment of male and female connectors with an electrically activated access valve.

Shown in the embodiment of FIG. 4, the conductive element 22 is a band, located on a base 42 of the male connector 12. This placement also ensures it will not interfere with the fluid passage 20. If the conductive element 22 is located on the base 42, the contacts 34 of the female connector 24 are correspondingly arranged around a base 60 of the female connector 24. Thus, the conductive element 22 will interact with the contacts 34, completing the circuit, upon complete insertion of the male connector 12 into the female connector 24.

Figure 5:
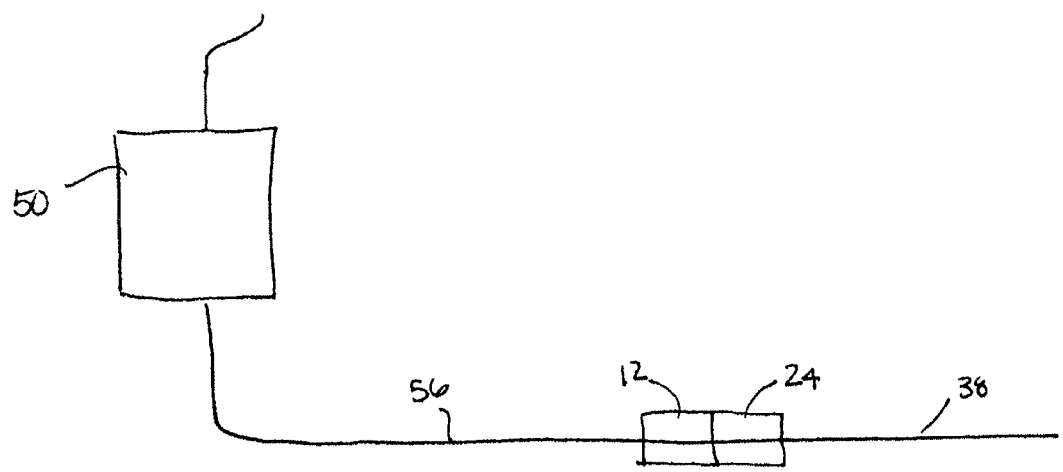
FIG. 5 is a side-view of another embodiment of male and female connectors with an electrically activated access valve, a pump, and tubing.

FIG. 5 shows another embodiment of the electrically activated access valve arrangement 10. As shown in FIG. 5, a pump 50 provides the electrical signal that is sent through wires 52 (not shown) which are embedded within tubing 56. The pump 50 may be used for an epidural or intravenous fluid administration. Embedding wires 52 within the tubing 56 protects them and allows for connection with a particularly sensitive line. The tubing 56 is connected to the male and female connectors 12, 24. The line 38 is connected to the female connector 24 and transfers fluid to a patient.

Figure 6:
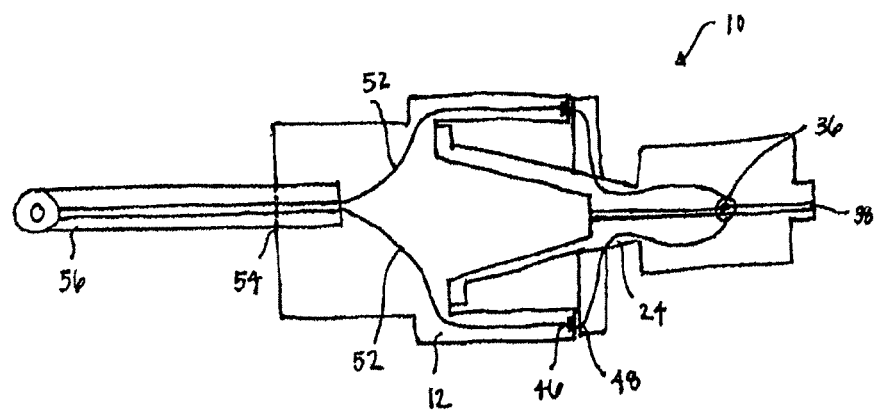
FIG. 6 is a partial-cross-sectional view of FIG. 5.

The male connector 12 in the embodiment of FIG. 6 comprises at least one connection port 46. The female connector 24 also includes at least one corresponding connection port 48. FIG. 6 shows the male connector 12 including two connection ports 46, and the female connector 24 including two corresponding connection ports 48. However, it is contemplated that the male and female connectors 12, 24 may comprise a plurality of corresponding connection ports 46, 48. When the male connector 12 is inserted into the female connector 24, the connection ports 46, 48 engage, and complete a circuit. This sends an electrical signal to the valve 36, which is connected to the female connector 24 by the line 38. The valve 36 is electronically controllable. The engagement of the connection ports 46, 48 allows for this control. Thus, the electrical signal causes the valve 36 to transition from its normally closed position to an opened position, allowing for an epidural or intravenous fluid administration through the line 38, to a patient. It is contemplated that in another embodiment, the valve 36 may be connected to the male connector 12. If it is desired, the male connector 12 may be removed from the female connector 24. This disconnects the completed circuit, and returns the valve 36 to its normally closed position. As shown in FIG. 6, the wires 52 run from the pump 50, through the tubing 56, through the male connector 12, and terminate at the connection port 46.

The solutions presented above may also be embodied in the following method. A method of controlling fluid flow from a fluid source to a patient includes a first step of connecting the male connector 12 and the female connector 24. When physically connected, the male and female connectors 12, 24 together form an electrical connection. A second step includes opening the electrically activated valve 36. This allows for fluid flow from the fluid source 58 to the patient only upon the connection of the male and the female connectors 12, 24, of the formation of the electrical connection. It would be apparent to one skilled in the art that this method provides another solution to the problem of misconnection of male and female luer connectors.

In sum, the present disclosure provides for an electrically activated access valve arrangement, comprising a male connector, a female connector, and a valve. In one embodiment, the male connector includes a conductive element, and the female connector includes contacts. Insertion of the male into the female connector completes a circuit, enabling an electrical signal to be sent to the valve. The electrical signal transitions the valve from the normally closed position to the opened position. In another embodiment, the male connector has a connection port which connects to a connection port of the female connector. A pump, such as an infusion pump, sends an electrical signal through the connection ports, which causes the valve to transition from the normally closed position to the opened position. As such, the connectors of the present disclosure will not function with typical male and female luer connectors. This prevents misconnection of the wrong line to a patient, while requiring no additional precautionary steps from busy medical personnel.

Although the present invention has been described and illustrated in detail, it is to be clearly understood that the same is by way of illustration and example only and is not to be taken by way of limitation.

What is claimed is:

1. An electrically activated access valve arrangement comprising:
   a first connector comprising:
      a first body with a first fluid passage therethrough; and
      a conductive element disposed on the first body; and
   a second connector configured to mate with the first connector, the second connector comprising:
      a second body with a second fluid passage therethrough; and
      two contacts disposed on the second body and positioned such that the two contacts respectively engage the conductive element at separated points when the first and second connectors are mated, thereby completing a circuit between the two contacts; and
   a normally closed, electrically activated valve fluidically coupled to the second fluid passage and electrically coupled to the contacts, the valve configured to open only when the circuit is completed between the two contacts.

2. The arrangement of claim 1, wherein the valve opens automatically when the circuit is completed between the two contacts.

* * * * *